United States Patent [19]
Aita et al.

[11] Patent Number: 6,132,423
[45] Date of Patent: *Oct. 17, 2000

[54] PHOTODYNAMIC THERAPY SYSTEM AND METHOD

[75] Inventors: Michael Aita, Sunnyvale; Michael Buchin, Palo Alto, both of Calif.

[73] Assignee: Eli Lilly and Company, Indianapolis, Ind.

[ * ] Notice: This patent issued on a continued prosecution application filed under 37 CFR 1.53(d), and is subject to the twenty year patent term provisions of 35 U.S.C. 154(a)(2).

[21] Appl. No.: 08/897,812

[22] Filed: Jul. 21, 1997

Related U.S. Application Data

[63] Continuation of application No. 08/412,143, Mar. 28, 1995, abandoned.

[51] Int. Cl.[7] .................................................. A61F 7/00
[52] U.S. Cl. ................................. 606/7; 606/15; 606/16
[58] Field of Search .............................. 606/3–7, 9, 10; 607/89

[56] References Cited

U.S. PATENT DOCUMENTS

| | | |
|---|---|---|
| 4,773,899 | 9/1988 | Spears . |
| 4,860,743 | 8/1989 | Abela . |
| 5,019,075 | 5/1991 | Spears et al. ................................. 606/7 |
| 5,116,864 | 5/1992 | March et al. ............................. 514/455 |
| 5,188,634 | 2/1993 | Hussein et al. ............................ 606/16 |
| 5,222,953 | 6/1993 | Dowlatshahi .............................. 606/7 |
| 5,269,779 | 12/1993 | Sogawa et al. ............................. 606/7 |
| 5,320,617 | 6/1994 | Leach ........................................ 606/15 |
| 5,346,488 | 9/1994 | Prince et al. ................................ 606/7 |
| 5,354,293 | 10/1994 | Beyer et al. . |
| 5,366,456 | 11/1994 | Rink et al. ................................. 606/15 |
| 5,411,466 | 5/1995 | Hess ............................................ 606/7 |
| 5,417,653 | 5/1995 | Sahota et al. ................................ 606/7 |
| 5,419,777 | 5/1995 | Hofling ...................................... 604/264 |
| 5,435,307 | 7/1995 | Friauf et al. ............................. 128/665 |
| 5,437,660 | 8/1995 | Johnson et al. ............................. 606/16 |
| 5,464,404 | 11/1995 | Abela et al. ................................ 606/15 |
| 5,487,740 | 1/1996 | Sulek et al. ................................ 606/15 |
| 5,776,174 | 7/1998 | Van Tassel ................................ 606/15 |

FOREIGN PATENT DOCUMENTS

| | | |
|---|---|---|
| 0 311 295 A2 | 4/1989 | European Pat. Off. . |
| 0 629 380 A1 | 12/1994 | European Pat. Off. . |
| WO 92/17243 | 10/1992 | WIPO . |

*Primary Examiner*—Robert L. Nasser
*Attorney, Agent, or Firm*—Heller Ehrman White & McAuliffe LLP

[57] ABSTRACT

A method and catheter system for irradiating a body lumen wall which comprises providing an elongated, flexible radiation transmission member having an emitting portion at its distal end, advancing the emitting portion to an area adjacent the wall defining the patient's body lumen to be treated by irradiation, and directing radiation through the transmission member while moving the transmission member to cause the emitting portion to irradiate a length of the wall of the body lumen. The transmission member may be rotated independently or in conjunction with longitudinal movement to achieve either selective or uniform irradiation of the wall defining the body lumen. In one embodiment, this invention comprises an elongated flexible shaft, having an inflatable member disposed at the distal end. A radiation transmission member having an emitting portion on its distal end is slidably disposed within the elongated shaft so that the emitting portion resides within the inflatable member. The system is configured so that the emitting portion may travel at least along the length of the inflatable member by longitudinally moving the transmission member. Optionally, the emitting portion may be configured to transmit radiation in a particular radial direction and the transmission member may be configured to rotate axially within the lumen.

12 Claims, 1 Drawing Sheet

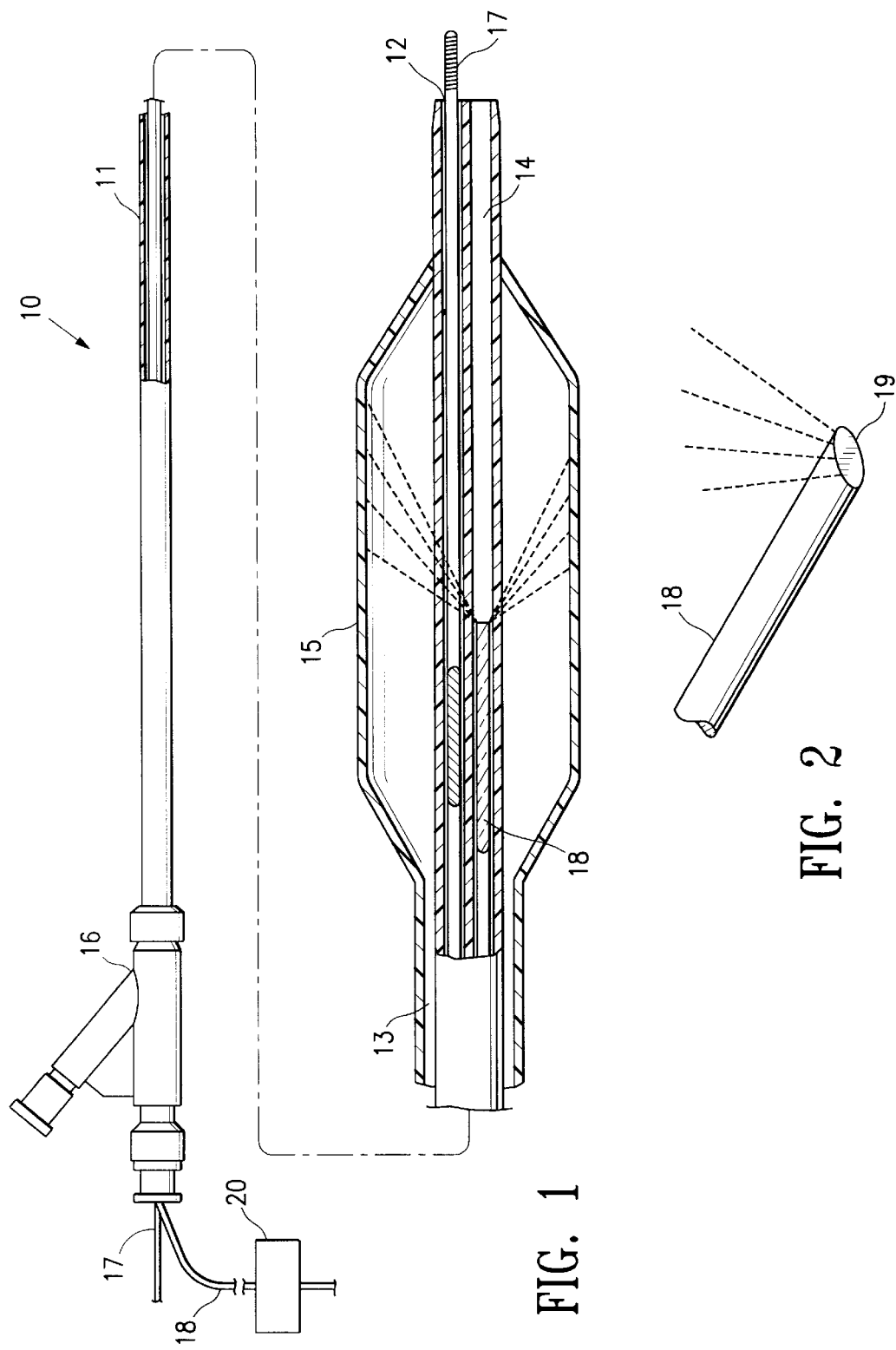

PHOTODYNAMIC THERAPY SYSTEM AND METHOD

This is a continuation of appplication Ser. No. 08/412,143 filed Mar. 28, 1995, now. U.S. Pat. No. 5,611,775.

BACKGROUND OF THE INVENTION

This invention is directed to the treatment of blood vessels affected by arteriosclerosis and more particularly to an assembly and method for preventing the restenosis of vessels following angioplasty comprising treating the vessel with a photoactivatable agent and selectively irradiating the treated area.

Arteriosclerosis is a common condition which occurs when atheromas, fatty-like substances, deposit in the blood vessels of a patient. Stenoses resulting from such deposits can seriously interfere with blood flow in the affected vessel, creating ischemic conditions distal to the stenosis. Balloon angioplasty procedures are a well known means for recanalizing stenosed vessels but currently suffer from a high rate of restenosis, requiring additional angioplasty or resort to other treatments such as atherectomy. Further, restenosis is also associated with these other means of treating arteriosclerosis.

Proliferation of smooth muscle cells resulting from the trauma to the vessel wall is thought to be a major factor in causing restenosis. Accordingly, many attempts to reduce restenosis have centered around inhibiting the growth of smooth muscle cells. U.S. Pat. No. 5,116,864 (March et al.), which is incorporated in its entirety by reference, discloses one promising technique. This reference teaches the use of photoactivatable psoralens to significantly inhibit the proliferation of smooth muscle cells following irradiation with long-wave ultraviolet light. In general, psoralen is administered to the patient orally, intravenously or via drug-delivery catheters such as disclosed in U.S. patent application Ser. No. 08/238,904, filed May 6, 1994, now U.S. Pat. No. 5,611,775, which are incorporated in their entirety by reference. Next, the stenosed area of the patient's vasculature is recanalized by angioplasty, atherectomy or other procedure. Finally, a catheter carrying an optical fiber is used to irradiate the recanalized area of the patient's vasculature with UV radiation having a wavelength of approximately 320 to 400 nm.

For this procedure to be effective, the irradiation of the recanalized area must effectively activate the psoralen. Accordingly, the catheter system used should provide either relatively uniform irradiation or selective irradiation as desired by the operator. U.S. Pat. No. 4,773,899 (Spears), which is incorporated in its entirety by reference, represents an example of a balloon catheter for delivering UV radiation in conjunction with photodynamic therapy. However, there are a number of drawbacks associated with the Spears catheter. The reference discloses only the simultaneous irradiation of all parts of the wall adjacent to the balloon. Achieving simultaneous, uniform irradiation is technically difficult. It often requires a complex interface at the distal end of the fiber to provide uniform diffusion of the emitted radiation. Generally, the means for diffusing radiation at the end of the fiber increases the diameter of the optical fiber and correspondingly increases the overall outer diameter of the system. Alternatively, the means for diffusing radiation involves removing the protective sheath and cladding from a distal portion of the optical fiber, making the fiber susceptible to breakage. There also may be conditions which make it desirable to selectively irradiate the vessel, for example, when there is an asymmetric lesion. The Spears catheter and the other prior art devices do not offer this capability.

What has been needed is a simple catheter system and method for either uniformly or selectively supplying an effective amount of radiation to activate administered psoralen or other photoactivatable therapeutic agents which is easy to manufacture. There is also a need for a radiation transmission and emitting means which has a small profile. This invention satisfies these and other needs.

SUMMARY OF THE INVENTION

This invention provides a method for treating a wall defining a patient's body lumen by irradiation comprising the steps of providing an elongated, flexible radiation transmission means having an emitting portion at its distal end, advancing the radiation transmission means within the patient's body lumen until the emitting portion is adjacent an area of the wall defining the body lumen to be treated by irradiation, and directing radiation through the transmission means while moving the transmission means to cause the emitting portion to irradiate a length of the wall of the body lumen. In a preferred embodiment, the radiation transmission means is moved longitudinally within the body lumen. If desired, the emitting portion of the transmission means may be configured to bias the radiation in a particular radial direction. When using a transmission means having this feature, the transmission means may be rotated independently or in conjunction with longitudinal movement to achieve either selective or uniform irradiation of the wall defining the body lumen.

One embodiment of a device useful in the practice of this invention comprises an elongated flexible shaft having an inflatable member disposed at the distal end. The radiation transmission means having an emitting portion on its distal end is slidably disposed within an inner lumen of the elongated shaft so that the emitting portion generally resides within the inflatable member. The system is configured so that the emitting portion may travel at least along the length of the inflatable member by longitudinally moving the transmission means within the inner lumen. Optionally, the emitting portion may be configured to transmit radiation in a particular radial direction and the transmission means may be configured to also rotate within the lumen.

Preferably, the emitting portion may comprise the cut end of the transmission means so that radiation is emitted in a cone. One advantage of this design is a minimized outer diameter. Accordingly, such transmission means may be incorporated into balloon angioplasty catheter while maintaining an overall low system profile.

BRIEF DESCRIPTION OF THE DRAWINGS

FIG. 1 is a longitudinal elevational view, partially in section, of a photodynamic therapy system of this invention.

FIG. 2 is an elevational view of an emitting portion of a radiation transmission means configured to emit radiation in a biased radial direction.

DETAILED DESCRIPTION OF THE DRAWINGS

FIG. 1 illustrates a photodynamic therapy system 10 embodying features of the invention which generally include an elongated flexible shaft 11 having a guide wire lumen 12, an inflation lumen 13, a radiation transmission means lumen 14 and an inflatable member 15 on a distal portion of shaft 11 in fluid communication through the inflation lumen 13 with an adaptor 16 at the proximal end of shaft 11. A guidewire 17 is slidably disposed within guidewire lumen 12. A radiation transmission means 18 having emitting portion 19 on the distal end is slidably disposed within lumen 14. Emitting portion 19 may travel longitudinally through the portion of lumen 14 which resides within inflatable member 15. The proximal portion of radiation transmission means 18 extends out the adaptor 16 and is operatively connected to a radiation generating means (not shown). For generating UVA radiation, an argon laser is suitable. The system is configured so that appropriate longitudinal movement of radiation transmission means 18 causes emitting portion 19 to travel the length of balloon member 15.

Radiation transmission means 18 generally comprises a conventional optical fiber having low attenuation for the wavelength of the radiation to be transmitted, but other wave guides may be suitable. Photoactivation typically requires energy delivery only on the order of milliwatts, so a single fiber usually has sufficient diameter to transmit the requisite energy while maintaining flexibility to traverse tortuous regions of the body lumen.

In a preferred embodiment, emitting portion 19 is formed by simply cutting the optical fiber. In such embodiments, it is desirable to maximize the numerical aperture of the fiber so that radiation is emitted in a cone having an apex as large as practical. Fibers suitable for transmitting ultraviolet wavelength having a numerical aperture of 0.37 and a corresponding emission cone of approximately 43° are available. Shorter fiber lengths may enable higher numerical apertures. The emitted radiation is further scattered by the lumen 14 and the inflatable member 15. Alternatively, the emitting portion 19 could comprise a lens or other means for diffusing light or could comprise a treated portion of transmission means 18, for example an abraded or decladed portion. Treating the transmission member can weaken the treated portion and generally increases the manufacturing difficulties. On the other hand, such treatment can cause the emitting portion to transmit a greater proportion of the radiation in a lateral direction towards the wall of the body lumen or to transmit the radiation in a particular radial direction. FIG. 2 illustrates the emitting portion 19 of radiation transmission means 18 in which a bare portion of an optical fiber has been cut at a 45° angle and the cut end has been mirrored.

These features in conjunction with longitudinal movement of the transmission means allow increased control over dosimetry. For example, the embodiment shown in FIG. 2 transmits radiation in a biased radial direction. Preferably, transmission means 18 should be rotatably disposed within lumen 14 to allow the axial rotation of emitting portion 19 within inflatable member 15. Thus, by appropriate rotation and/or longitudinal movement of the radiation transmission means 18, the wall defining the body lumen adjacent inflatable member 15 may be selectively or uniformly irradiated.

Generally, inflatable member 15 is configured to displace blood to allow transmission of radiation from the emitting portion 19 to the wall defining the body lumen adjacent the inflatable member 15. Inflatable member 15 should be relatively transparent to the wavelength of the radiation used, but otherwise may be formed in a conventional manner. Inflatable member 15 may further comprise perfusion ports and lumens in a conventional manner to allow treatment without causing downstream ischemic conditions. In some embodiments, inflation member 15 is configured to carry out an angioplasty procedure. This allows dilatation and subsequent irradiation to be performed without introducing separate devices. However, it may be desirable to configure inflatable member 15 to displace blood only, requiring only low pressure inflation and allowing the use of materials having optimal transmission characteristics. In these embodiments, a separate angioplasty balloon could be carried on another portion of the elongated shaft 11 to allow both procedures to be performed using the same device.

The method of using the photodynamic therapy systems of this invention generally follows conventional practices. In particular, the system 10 may be located by first introducing a guiding catheter (not shown) having a preshaped distal tip percutaneously in the patient's arterial system using the conventional Seldinger technique and advancing it until the preshaped distal tip is seated in the ostium of the desired artery. A guidewire 17 is backloaded into guidewire receiving lumen 13, and both the guidewire and the system 10 are advanced together through the guiding catheter to its distal end. The guidewire 17 is advanced out the guiding catheter through the patient's vasculature via fluoroscopic imaging until it crosses the target area. Then the system 10 is advanced over the guidewire 17 until the inflatable member 15 is positioned across the area. The inflatable member 15 is inflated to displace blood and facilitate transmission of radiation. Emitting portion 19 is disposed within lumen 14 just distal of inflatable member 15. Radiation is then supplied through radiation transmission means 18 while transmission means 18 is pulled back through lumen 14 at a controlled rate. The controlled pull may be achieved by a control means 20. For example, a stepper motor may be operatively connected to transmission means 18, but other means are also suitable. Once emitting portion 19 has traveled to an area of lumen 14 proximal to inflatable member 15, a uniform dose of radiation has been supplied to the tissue adjacent the inflatable member 15.

System 10 may be used in any application to deliver radiation of a desired wavelength to a region within a patient's vasculature. In particular, this may include the activation of any photoactivatable agent, including porphyrins, phthalocyanine compounds and psoralens. System 10 has been shown to be effective in inhibiting smooth muscle cell proliferation following angioplasty in rabbits (Spaedy, T J et al., unpublished manuscript). Rabbits given a systemic administration of 8-methoxypsoralen to a serum level of about 1 $\mu$M followed by irradiation with 10 J/cm$^2$ of 351 nm UVA in conjunction with angioplasty demonstrated inhibition of smooth muscle proliferation compared to rabbits undergoing angioplasty alone, angioplasty followed by irradiation or angioplasty followed by systemic administration of psoralen.

Photoactivation of psoralens generally requires radiation having a wavelength between about 320 nm and 400 nm. Other photoactivable agents require wavelengths specific to the agent. Concerns about UV toxicity in particular may make longer wavelengths desirable. In particular, wavelengths between 400 nm and 900 nm, corresponding to laser diode activation, may also be used.

Although it has been described primarily with reference to presently preferred embodiments, one skilled in the art should recognize that various modifications and improvements are within the scope of this invention.

What is claimed is:

1. A method for treating an arterial wall of a patient's coronary, comprising:

a) providing an elongated flexible shaft having an inflation lumen, a distally open guidewire lumen for receiving a guidewire therein, a distally sealed radiation transmission member lumen, an inflatable member on a distal portion of the shaft in fluid communication with the inflation lumen and a radiation transmission member having emitting portion configured to emit radiation in a substantially lateral direction slidably disposed within the radiation transmission member lumen;

b) advancing the elongated flexible shaft through the artery to a location therein;

c) inflating the infl atable m ember to displace blood from the location;

d) directing radiation through the radiation transmission member, and emitting radiation passing through the radiation transmission member through the emitting portion and the inflated inflatable member, with a substantial amount of the emitted radiation being directed to and impinging on the tissue of the arterial wall; and e) moving the radiation transmission member within the artery as radiation is emitted from the emitting portion to irradiate the arterial wall.

2. The method of claim 1 further comprising the step of moving the radiation transmission member longitudinally within the artery as radiation is emitted from the emitting portion to irradiate the arterial wall.

3. The method of claim 2 wherein a control member is operatively connected to the radiation transmission member to move the transmission member at a controlled rate.

4. The method of claim 3 further comprising the step of rotating the radiation transmission member within the artery as radiation is emitted from the emitting portion to irradiate the arterial wall.

5. The method of claim 1 further including the step of incorporating a photoactivatable agent into tissue of the arterial wall which continues to act after exposure to radiation.

6. The method of claim 5 wherein the photoactivatable agent comprises a psoralen, further comprising the step of directing radiation having a wavelength between about 320 nm and about 400 nm through the radiation transmission member.

7. The method of claim 5 wherein the step of activating the photoactivatable agent further comprises directing radiation having a wavelength between about 400 to about 900 nm on the tissue of the arterial wall.

8. The method of claim 1 wherein the inflatable member is configured to perform an angioplasty procedure, further comprising the step of inflating the inflatable member within the artery to perform an angioplasty procedure therein.

9. A method for treating an arterial wall of a patient's coronary artery after a procedure has been performed therein to prevent the restenosis of the arterial wall, comprising:

a) providing an elongated flexible shaft having an inflation lumen, a distally open guidewire lumen for receiving a guidewire therein, a distally sealed radiation transmission member lumen, an inflatable member on a distal portion of the shaft in fluid communication with the inflation lumen and a radiation transmission member having emitting portion configured to emit radiation in a substantially lateral direction slidably disposed within the radiation transmission member lumen;

b) advancing the elongated flexible shaft through the artery to a location therein;

c) inflating the inflatable member to displace blood from the location;

d) directing radiation through the radiation transmission member, and emitting radiation passing through the radiation transmission member through the emitting portion and the inflated inflatable member, with a substantial amount of the emitted radiation being directed to and impinging on the tissue of the arterial wall after the procedure has been performed therein; and e) moving the radiation transmission member within the artery as radiation is emitted from the emitting portion to irradiate the arterial wall.

10. The method of claim 9 further including the step of incorporating a photoactivatable agent into tissue of the arterial wall such that the radiation directing step activates the photoactivatable agent which acts during and after the radiation exposure.

11. A method for treating an arterial wall of a patient's coronary artery after an angioplasty procedure has been performed therein to prevent the restenosis of the arterial wall, comprising:

a) providing an elongated shaft having a proximal end, a distal end, an inflation lumen extending distally to a location spaced proximal to the distal end of the shaft, a distally open guidewire lumen for receiving a guidewire therein, and a probe lumen extending distally beyond the inflation lumen and having a closed distal end, an inflatable member on a distal shaft section having an interior, which is defined at least in part by a wall, in fluid communication with the inflation lumen, an elongated probe member slidably disposed within the probe lumen and having a distal end configured to emit radiation so as to irradiate the patient's tissue at the desired location;

b) advancing the elongated shaft through the artery to a location therein;

c) inflating the inflatable member to displace blood from the location;

d) directing radiation through the elongated probe member, and emitting radiation passing through the elongated probe member through the radiation emitting distal end and the inflated inflatable member, with a substantial amount of the emitted radiation being directed to and impinging on the tissue of the arterial wall after the procedure has been performed therein; and e) moving the elongated probe member within the artery as radiation is emitted from the radiation emitting distal end to irradiate the arterial wall.

12. The method of claim 11 further including the step of incorporating a photoactivatable agent into the tissue of the arterial wall such that the radiation directing step activates the photoactivatable agent which acts during and after the radiation exposure.

* * * * *